(12) United States Patent
Yu

(10) Patent No.: US 7,355,038 B2
(45) Date of Patent: Apr. 8, 2008

(54) PHASE ISOLATION PROCESS FOR BIOMACROMOLECULE COMPONENTS

(75) Inventor: Weiming Yu, Hangzhou (CN)

(73) Assignee: V-Gene Biotechnology Limited, Hangzhou (CN)

( * ) Notice: Subject to any disclaimer, the term of this patent is extended or adjusted under 35 U.S.C. 154(b) by 214 days.

(21) Appl. No.: 10/948,258

(22) Filed: Sep. 24, 2004

(65) Prior Publication Data

US 2005/0106604 A1    May 19, 2005

(30) Foreign Application Priority Data

Nov. 14, 2003    (CN) .................. 2003 1 01086497

(51) Int. Cl.
 *C07H 21/00* (2006.01)
(52) U.S. Cl. ............... 536/25.41; 536/25.4; 536/25.42
(58) Field of Classification Search .................... None
See application file for complete search history.

(56) References Cited

U.S. PATENT DOCUMENTS

| | | | | |
|---|---|---|---|---|
| 3,657,118 A | * | 4/1972 | Kraffczyk et al. | .......... 210/658 |
| 4,661,454 A | * | 4/1987 | Botstein et al. | ........ 435/254.21 |
| 5,446,024 A | * | 8/1995 | Builder et al. | ................. 514/12 |
| 5,840,858 A | * | 11/1998 | Smith et al. | ................. 530/413 |
| 6,713,618 B1 | * | 3/2004 | Yanai et al. | ............. 536/23.51 |
| 7,053,054 B2 | * | 5/2006 | Paradisi et al. | ................ 514/16 |

FOREIGN PATENT DOCUMENTS

WO    WO 01/07599 A1    2/2001

OTHER PUBLICATIONS

Adams et al., "Levels of translatable mRNAs for cell surface protein, collagen precursors, and two membrane proteins are altered in *Rous sarcoma* virus-transformed chick embryo fibroblasts," Proc.Natl.Acad.Sci., Aug. 1977, vol. 74, No. 8, pp. 3399-3403.*
Braga et al., "Comparison of Yield, Composition, and Antioxidant Activity of Turmeric (*Curcuma longa* L.) Extracts Obtained Using Various Techniques," Journal of Agricultural and Food Chemistry, Jul. 2003, vol. 51, pp. 6604-6611.*

(Continued)

*Primary Examiner*—Kenneth R. Horlick
*Assistant Examiner*—Molly Baughman
(74) *Attorney, Agent, or Firm*—Birch, Stewart, Kolasch & Birch, LLP

(57) ABSTRACT

The present invention relates to a phase isolation process for biomacromolecule components, after pretreating the substance to be isolated: 1) adding sufficient amount of buffer (one of the compound selected from ammonium sulfate, cesium chloride, sodium sulfate, and ethylenediamine tetraacetic acid) and homogenizing gently to carry out agglutination; 2) adding phase isolation solution (one compound or a mixture of more compound selected from the group consisting of ethanol, isopropyl alcohol, isobutyl alcohol and acetone) and homogenizing gently, centrifuging to form an upper phase and a lower phase to carry out phase isolation; wherein lipid is in the upper phase, protein precipitates in the phase middle, DNA plasmid, viral nucleic acid, mitochondrial DNA are in the lower phase, and total RNA precipitates in the lower phase; genomic DNA precipitates in the lower phase or in the phase middle together with protein. The production yield and purity of isolating components are high in the present invention, providing advantageous condition for purifying these components.

6 Claims, 4 Drawing Sheets

OTHER PUBLICATIONS

Nelson et al., "Purification of Cloned and Genomic DNA by Guanidine Thiocyanate/Isobutyl Alcohol Fractionation," Analytical Biochem., 1992, vol. 207, pp. 197-201.*

Silk et al., "Darkness and antibiotics increase the steady-state transcripts of the elongation factor gene (tuf) in *Chlamydomonas reinhardtii*," Current Genetics, 1988, vol. 14, pp. 119-126.*

Sambrook et al., Molecular Cloning: A Laboratory Manual, 2nd Edition, Cold Spring Harbor Laboratory Press, 1989, vol. 1, pp. 7.19-7.25.*

Scopes, Robert K., Protein Purification: Principles and Practice, 3rd Edition, Springer-Verlag New York, Inc., 1994, pp. 76-93, 324-335, and 346-348.*

* cited by examiner

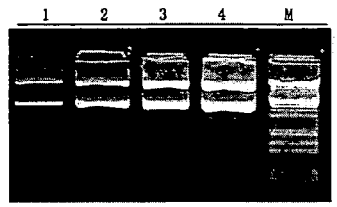
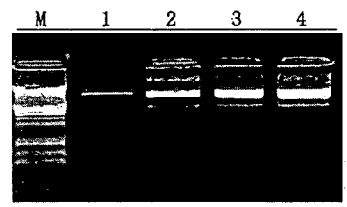
Fig. 2-1    Fig. 2-2
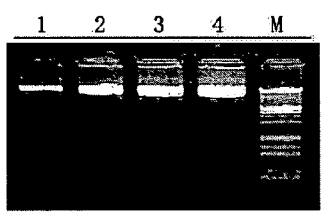
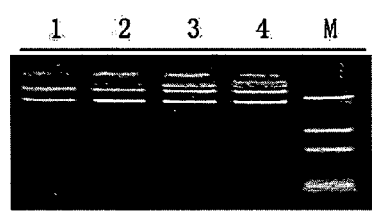
Fig. 2-3    Fig. 2-4
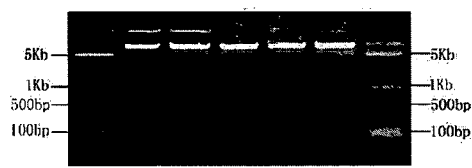
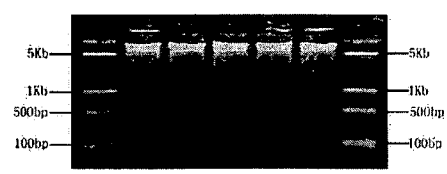
Fig. 3-1    Fig. 3-2

Fig. 3-3  Fig. 3-4
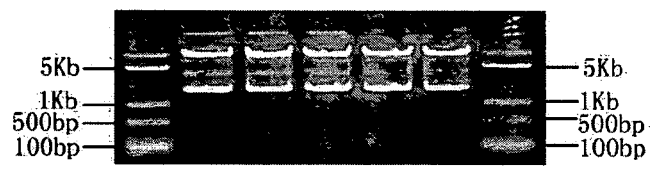
Fig. 3-5
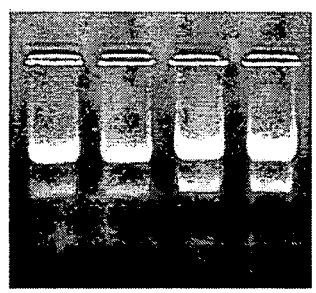
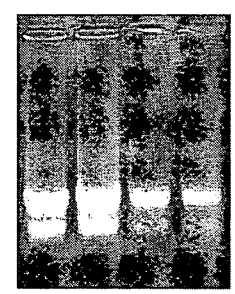
Fig. 4-1  Fig. 4-2

PHASE ISOLATION PROCESS FOR BIOMACROMOLECULE COMPONENTS

This Nonprovisional application claims priority under 35 U.S.C. §119(a) on Patent Application No(s). 2003101086497 filed in China on Nov. 14, 2003, the entire contents of which are hereby incorporated by reference.

TECHNICAL FIELD

The present invention relates to a two-phase isolation process for biomacromolecule components, which separates biomacromolecule components including protein, lipid, DNA (plasmid, viral nucleic acid, mitochondrion, genome) and total RNA for isolating.

BACKGROUND

The most effective means for isolating biomacromolecule are chromatography and capillary electrophoresis at the present time. In conventional process for purifying biomacromolecule, reagents such as SDS (sodium dodecyl sulfate), TX-100, CTAB (cetyl trimethylammonium bromide, CTAB), guanidine hydrochloride, GuSCN (guanidinium isothiocyanate) and the like are used to lyse the cells, so that polysaccharide, plasmid DNA, and RNA are extracted into the upper phase and protein is denatured and precipitated in the phase middle or is distributed into the phase middle partly. But still a small amount of high hydrophilic protein is distributed into the upper phase, and components cannot be isolated effectively and quickly from each other. Genomic DNA and lipid are released into the supernatant, and then protein is extracted and removed by phenol and chloroform (toxic), finally plasmid DNA is precipitated in the presence of ethanol or isopropyl alcohol and is recovered. However, a large amount of protein, lipopolysaccharide and polysaccharide are remained in such purified plasmid DNA, and they make a bad influence on many important biological experimental results. More particularly, biological researches such as cell transfection, gene treatment, DNA bacterin immunity and the like have higher requirement on the purity of plasmid DNA, and such a process hardly obtains a desired purity and other purifying processes are to be used to isolate and purify plasmid DNA.

Purifying plasmid DNA with DEAE-silica resin has been disclosed in another document. There is phosphate radical in DNA molecule and thus makes it negative. The density of DEAE group on silica is substantially higher than that on conventional polysaccharides resin, which makes DNA combined to the resin with high DEAE density more firmly and very high salt concentration is necessary to elute DNA. But other impurities such as protein can be eluted in lower salt concentration so as to be isolated from DNA entirely. Such a case will occur only when anions such as SDS (sodium dodecyl sulfate) are not combined to the surface of biomacromolecule. However, in fact, a large amount of denatured protein, LPS, and polysaccharide combined with SDS is remained in the supernatant containing plasmid DNA. SDS molecule has sulfate radical on it and shows negative, and can combine with molecules such as protein firmly resulting in carrying plentiful negative charges on the surface of these molecules, which changes the original chromatography activity to a great extent and makes an essential change on the elution conditions of protein, LPS and polysaccharide, and it is difficult to isolate DNA from impurities such as protein, LPS thoroughly.

Chinese patent application CN 1378592A has disclosed a process for purifying plasmid DNA using tangential flow filtration without RNA enzyme and organic solvent, the process comprising: (a) digesting the cells; (b) culturing the cells for 4~24 hours for lysing and dissolving, but not enzymatic digesting RNA; (c) removing lysing impurity from the cells for providing a solution of plasmid DNA; (d) filtrating the solution by tangential flow filtration means so as to obtain reflux solution containing plasmid DNA; (e) recovering the reflux solution. The undesired result has been gained in the isolating speed and effect by using the above process.

DESCRIPTION

The technical problem to be solved in the present invention is to provide a phase isolation process capable of isolating biomacromolecule components, such as protein, lipid, DNA (plasmid, viral nucleic acid, mitochondrion, genome), and total RNA at one time, and overcome the defects of the background art.

A phase isolation process for biomacromolecule components, pretreating the substance to be isolated correspondingly, wherein the process comprising:

1) adding sufficient amount of buffer and homogenizing gently, the buffer being at least one compound selected from the group consisting of ammonium sulfate, cesium chloride, sodium sulfate, and ethylenediamine tetraacetic acid so as to carry out agglutination;

2) adding phase isolation solution and homogenizing gently, centrifuging to form an upper phase, a lower phase, phase middle precipitation, and lower phase precipitation; wherein lipid is in the upper phase, protein precipitates in the phase middle, DNA plasmid, viral nucleic acid, mitochondrial DNA are in the lower phase, and total RNA precipitates in the lower phase; genomic DNA precipitates in the lower phase or in the phase middle together with protein; the phase isolation solution is at least one compound selected from the group consisting of ethanol, isopropyl alcohol, isobutyl alcohol and acetone so as to carry out phase isolation;

wherein isolation for purifying total RNA, carrying out a pre-phase isolation and purifying process before step 2), comprising: adding pre-phase isolation solution of isobutyl alcohol and homogenizing gently, centrifuging, phase forming, discarding protein in the phase middle, taking the lower phase, and entering into step 2).

Steps 1) and 2) are a new phase isolation system. In this system, salt highly insoluble in at least one compound selected from the group of ethanol, isopropyl alcohol, isobutyl alcohol and acetone must exist, and protein, LPS (bacterial lipid polysaccharide), RNA and lipid will be denatured and separated out or not dissolved in the salt, whereas DNA must be dissolved in it completely. And ammonium sulfate, cesium chloride, sodium sulfate and ethylenediaminetetraacetic acid have this feature. Ammonium sulfate is preferable for its low price and effective denaturant for protein, LPS and RNA. In the system, after the cells are dissolved in the presence of SDS/NaOH, CATB, guanidine hydrochloride, GuSCN and carbamide and plasmid DNA is released, the cells are neutralized by the solution containing ammonium sulfate, and protein is denatured and combined with genomic DNA to form compact insoluble composition (when the system is alkaline, genomic DNA transfers to the lower phase). But meanwhile the concentration of ammonium sulfate in the solution system is not enough to precipitate other impurities effectively. After added mixed organic solvent containing ethanol and isopropyl alcohol, water is extracted into the upper phase, and a near saturation of the concentration of ammonium sulfate in the inorganic phase occurs and dehydration appears in it. Except plasmid DNA, genomic DNA, mitochondrial DNA and viral DNA are still in solubility and locate in the lower phase, fat soluble components of the cells are extracted into the upper phase, and all other components of the cells are denatured and precipitated for insoluble to saturated ammonium sulfate and mixed solvent containing ethanol and isopropyl alcohol. RNA is centrifuged to precipitate at the bottom of tube for its high density and protein precipitates in the phase middle.

Water in ammonium sulfate solution is extracted after adding mixed solvent containing ethanol and isopropyl alcohol, and a near saturated ammonium sulfate solution in the lower phase is obtained. The key for forming the two-phase system is: (1) a solution containing a certain concentration of ammonium sulfate; (2) a mixed solvent containing ethanol and isopropyl alcohol in a certain volume and ratio. If the concentration is too low, it is difficult to form the two phases and the ammonium sulfate will be separated out; if the concentration is too high, the ammonium sulfate will be separated out too. According to the experiments, the two-phase system will be formed only by adding appropriate ratio and volume of ethanol and isopropyl alcohol mixed solvent, and a near saturation of the concentration of ammonium sulfate in the lower phase is obtained. If the volume of the mixed solvent is too small, phases will not be formed and the ammonium sulfate will be separated out; and if the volume of the mixed solvent is too big, precipitation will be formed without DNA isolating, but it is not good for the later process. The two-phase system may be formed using ethanol in ammonium sulfate solution, but the volume of ethanol is too big and any mistakes in the ratio will cause phases not formed or ammonium sulfate deposited and separated out. Certain amount of isopropyl alcohol will widen the ratio range of ammonium sulfate solution to organic solvent containing ethanol and isopropyl to a great extent.

According to the different objects, the components to be purified are different, the components of the buffers and the ratio of two alcohols in the phase isolation solution will be different so as to increase the production yield and purity. The value of pH of the solution system can be regulated and controlled by the adding amount of phosphate and acetate.

1. Isolation for purifying plasmid DNA. The buffer is prepared by dissolving 380~480 g ammonium sulfate or cesium chloride and 14~18 g monosodium orthophosphate in water and bringing the volume to 1 liter; phase isolation solution for purifying plasmid DNA is the mixture of ethanol and isopropyl, the ratio of volume is ethanol: isopropyl alcohol=2:1~10:1; and the solution system is acidic.

Preferably, 10~60 g of ammonium acetate is added into the buffer for facilitating salting out.

Advantageously, the solution is acidic and the value of pH is 5~6.7.

In practical operation, the desired effect will be achieved by adding the buffer and the phase isolation solution, the ratio of volume is buffer: phase isolation solution=1.6~2.4: 2.6~3.2 in steps 1) and 2), when suspending step finished and the volume is unit volume.

2. Isolation for purifying genomic DNA. The buffer is prepared by dissolving 330 g of ammonium sulfate in water and bringing the volume to 1 liter; the phase isolation solution for purifying genomic DNA is the mixture of anhydrous ethanol and isopropyl alcohol, the ratio of volume is anhydrous ethanol: isopropyl alcohol=0.5:1~2:1; and the solution system is alkaline, the value of pH is 7.5~9.0 advantageously.

The phase isolation solution further contains 2~5 ml/l glacial acetic acid.

3. Isolation for purifying total RNA. The pre-phase isolation solution is isobutyl alcohol, the production yield of total RNA can be increased 10% ~50% after the pre-phase purifying process; the buffer is prepared by dissolving 398 g ammonium sulfate, 96 g guanidine hydrochloride, 4 g $Na_2HPO_4.12H_2O$ in water and bringing the volume to 1 liter; the phase isolation solution is the mixture of ethanol and isopropyl alcohol, the ratio of volume is ethanol: isopropyl alcohol=7:5~7:7, and the value of pH is 6.8±0.05 advantageously.

4. Isolation for protein. The buffer is ammonium sulfate of 90% ~100% saturation; the phase isolation solution for purifying protein is the mixture of anhydrous ethanol and isopropyl alcohol, the ratio of volume is anhydrous ethanol: isopropyl alcohol=1:3~1:10.

The buffer further contains 80 mM monosodium orthophosphate and 80 mM sodium orthophosphate dimetallic; the phase isolation solution further contains 2~5 ml/l glacial acetic acid.

Precooling said phase isolation solution will bring better phase isolation effect, and the precooling temperature is not higher than 10° C. generally.

In the novel phase isolation process of the present invention, different components of the cells can be separated out at the same time only in one step, and this is the innovation point of the present invention. As shown in FIG. 1, in the phase isolation system, RNA precipitates at the tube bottom 4 during centrifuge, the denatured protein forms insoluble composition and locates in the phase middle 2, polysaccharide, lipid polysaccharide, lipid, cell metabolite and pigment are extracted into the upper phase 1, plasmid DNA is still in solubility and locates in the lower phase 3, and genomic DNA deposits in the lower phase for the solution system being alkaline or deposits together with protein in the phase middle for the solution system being acidic.

BRIEF ILLUSTRATION OF DRAWINGS

FIG. 2-1 is an electrophoretogram of super pure plasmid DNA extracted from bacteria provided by Nankai University, wherein, 60 µl of eluted and purified plasmid DNA, and 4 µl thereof for electrophoresis, number 1, 2, 3, 4 indicates that the volume of the sample is 1 ml, 2 ml, 3 ml, 4 ml respectively;

FIG. 2-2 is an electrophoretogram of super pure plasmid DNA extracted from bacteria containing pPic-91C plasmid, wherein, 60 µl of eluted and purified plasmid DNA, and 4 µl thereof for electrophoresis, number 1, 2, 3, 4 indicates that the volume of the sample is 1 ml, 2 ml, 3 ml, 4 ml respectively;

FIG. 2-3 is an electrophoretogram of super pure plasmid DNA extracted from *Pseudomonas aeruginosa* (*P. aeruginosa*), wherein, 60 µl of eluted and purified plasmid DNA, and 4 µl thereof for electrophoresis, number 1, 2, 3, 4 indicates that the volume of the sample is 1 ml, 2 ml, 3 ml, 4 ml respectively;

FIG. 2-4 is an electrophoretogram of super pure plasmid DNA extracted from bacteria containing pET-2a plasmid, wherein, 60 µl of eluted and purified plasmid DNA, and 4 µl thereof for electrophoresis, number 1, 2, 3, 4 indicates that the volume of the sample is 1 ml, 2 ml, 3 ml, 4 ml respectively;

FIG. 3-1 is an electrophoretogram of genomic DNA extracted from 15 mg of mouse muscle tissue, wherein, 60 µl of eluted and purified plasmid DNA, and 4 µl thereof for electrophoresis;

FIG. 3-2 is an electrophoretogram of genomic DNA extracted from culturing cells, wherein, 60 µl of eluted and purified plasmid DNA, and 2 µl thereof for electrophoresis;

FIG. 3-3 is an electrophoretogram of genomic DNA extracted from 100 mg of holly leaf, wherein, 60 µl of eluted and purified plasmid DNA, and 2 µl thereof for electrophoresis;

FIG. 3-4 is an electrophoretogram of genomic DNA extracted from 150 µl of pig whole blood, wherein, 60 µl of eluted and purified plasmid DNA, and 4 µl thereof for electrophoresis;

FIG. 3-5 is an electrophoretogram of genomic DNA extracted from bacteria containing pUC-19 plasmid, wherein, 60 µl of eluted and purified plasmid DNA, and 4 µl thereof for electrophoresis;

FIG. 4-1 is an electrophoretogram of total RNA extracted from 0.4×10⁴ culturing cells, wherein, 40 µl of dissolved and purified total RNA, and 4 µl thereof for electrophoresis;

Figures 3, 4:
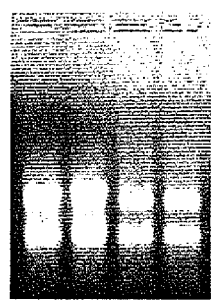
Figure 4:
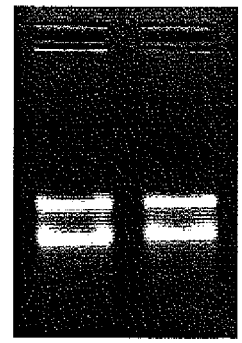
Figures 4, 5, 5A:
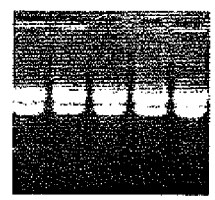
Figures 4, 5, 5B:
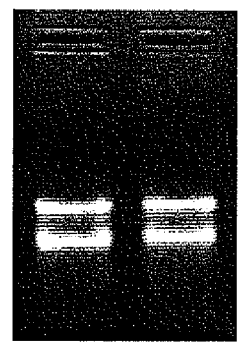
Figures 4, 5, 6:
Figures 4, 5, 6, 7:

FIG. 4-2 is an electrophoretogram of total RNA extracted from 200 mg of holly leaf, wherein, 200 µl of dissolved and purified total RNA, and 20 µl and 10 µl thereof for electrophoresis respectively;

FIG. 4-3 is an electrophoretogram of total RNA extracted from 250 µl of mouse whole blood, wherein, 40 µl of dissolved and purified total RNA, and 20 µl and 10 µl thereof for electrophoresis respectively;

FIG. 4-4 is an electrophoretogram of total RNA extracted from 3 ml of *Escherichia coli*, wherein, 40 µl of dissolved and purified total RNA, and 20 µl thereof for electrophoresis;

FIGS. 4-5(*a*) and 4-5(*b*) are electrophoretograms of total RNA extracted from 4 ml of yeast, wherein, 60 µl of dissolved and purified total RNA, and 20 µl thereof for electrophoresis;

FIG. 4-6 is an electrophoretogram of total RNA extracted from 100 mg of mouse liver, wherein, 100 µl of dissolved and purified total RNA, and 10 µl thereof for electrophoresis; and FIG. 4-7 is an electrophoretogram of total RNA extracted from 100 mg of mouse brain, wherein, 100 µl of dissolved and purified total RNA, and 10 µl thereof for electrophoresis

PREFERRED EMBODIMENTS

The present invention will be further described in details with reference to embodiments hereunder.

EXAMPLE 1

Phase Isolation for the Object of Purifying Plasmid DNA

Suspension: 25 mM Tris-HCl buffer containing RNase A1, 10 mM EDTA, and pH 8.0;

Lysing solution: 1% sodium dodecyl sulfate/0.18~0.2 M NaOH;

Buffer: 380~480 g ammonium sulfate or cesium chloride, 16~18 g monosodium orthophosphate, 36 g ammonium acetate, and add water to 1 liter.

Phase isolation solution: the mixture of ethanol and isopropyl alcohol, the ratio of volume is ethanol: isopropyl alcohol=2:1~10:1;

Generally, the ratio of volume is suspension: lysing solution: buffer: phase isolation solution=1:1:1.6~2.4:2.6~3.2.

RNase A1 is 100 µg/ml A1, enzyme component of RNA;

Tris is tris(hydroxymethyl)aminomethane;

EXAMPLE 1-1

Purifying for Small Amount of Super Pure Plasmid DNA

1. Preparation for Experiment

1) In the first use, all of the RNase A1 (100 µg/ml enzyme component of RNA) is added into bacteria suspension carried in the kit, homogenized, and stored in close condition at 4° C.

2) Prior to use, observe whether white precipitation appears in the bacteria lysing solution. If the precipitation exists, incubate and dissolve it gently at 37° C., and use it until it has been cooled to room temperature.

3) Precool and neutralize the buffer and phase isolation solution at 4C.

2. Steps of Process

Pretreatment: collect 1~4 ml overnight plasmid bacteria solution cultured in the LB culture medium, centrifuge at 12000×g for 30 seconds, and discard the supernatant completely. Suspend the bacteria precipitation fully with 250 µl bacteria suspension added with RNase A1.

Attention: excessive bacteria will influence lysing and neutralizing efficiency. If rich culture medium is used, the volume of the bacteria solution should be reduced half or more.

Attention: suspending should be uniform and little bacteria clump should not be remained, otherwise, lysing of bacteria will be affected.

Add 250 µl lysing solution (1% sodium dodecyl sulfate/ 0.2M of NaOH), reverse and blend for 4~6 times gently but fully, and the step should last for no longer than 5 minutes.

Attention: violently shaking is forbidden, otherwise, genomic DNA will be contaminated.

1) Agglutination: add 450 µl buffer cooled at 4° C. previously (420 g ammonium sulfate, 16 g monosodium orthophosphate, and add water to 1 liter), reverse for 8~10 times gently at once, and homogenize fully.

Attention: violently shaking is forbidden, otherwise, genomic DNA will be contaminated.

2) Phase isolation: add 650 µl phase isolation solution cooled at 4° C. previously (ethanol: isopropyl alcohol=3:1), reverse for 10 times gently, blend with more strength for several times so as to make the solution form a turbid emulsion, and centrifuge at 12000×g for 1 minute. Thus, upper phase in blue, colorless lower phase and ivory phase middle precipitation are formed. RNA precipitation at the tube bottom is not observed usually, because RNase A1 has been added in to digest and degrade RNA. Wherein, plasmid DNA waits for being purified in the lower phase.

Purifying for Small Amount of Super Pure Plasmid DNA

Figure 1:
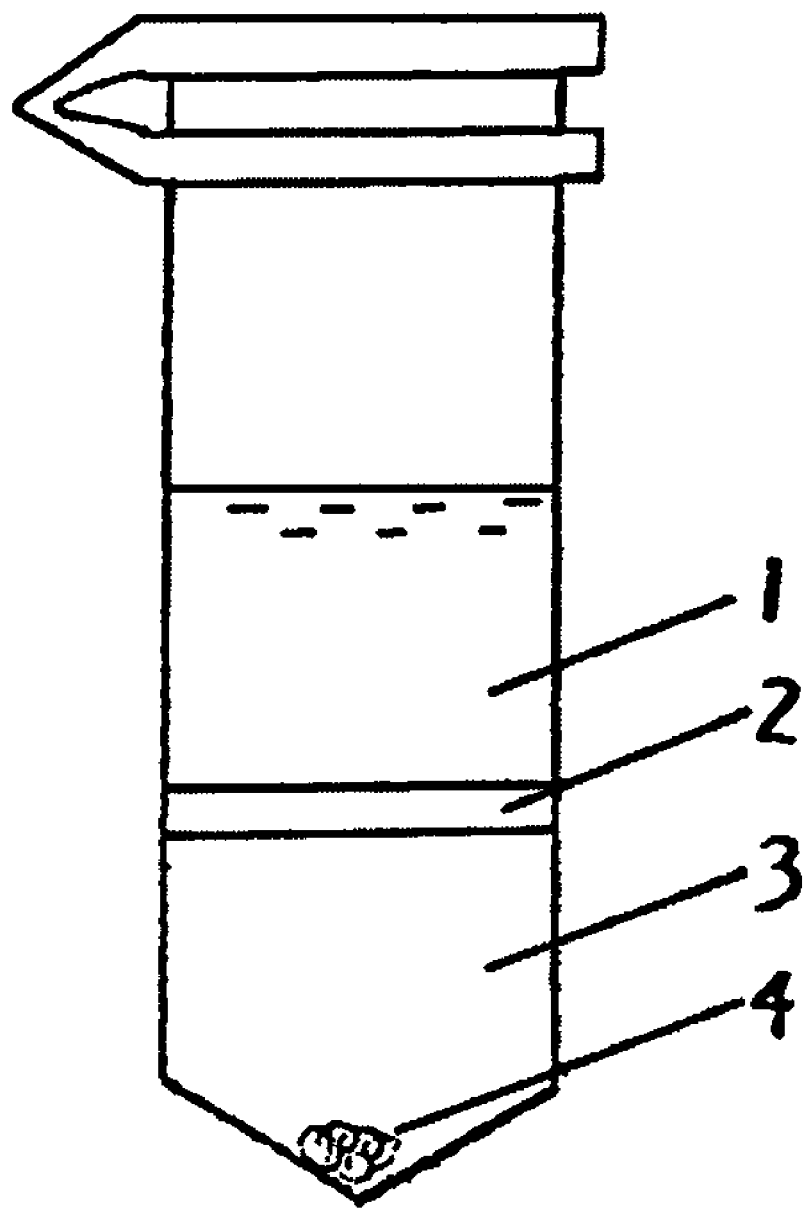
FIG. 1 shows a result of phase isolation.

| Sample | | The value of OD of super pure plasmid DNA | | | | Eluting Volume | Diluting Times | Electrophoretogram |
|---|---|---|---|---|---|---|---|---|
| Bacteria from Nankai University | Bacteria Volume (ml) | 1.0 | 2.0 | 3.0 | 4.0 | 60 μl | 4 | FIG. 2-1 |
| | $OD_{260}$ | 0.360 | 0.758 | 1.262 | 1.754 | | | |
| | $OD_{280}$ | 0.190 | 0.389 | 0.650 | 0.909 | | | |
| | $OD_{260}/OD_{280}$ | 1.89 | 1.95 | 1.94 | 1.93 | | | |
| | Concentration (ng/μl) | 18.0 | 38.0 | 62.0 | 87.0 | | | |
| | Production Yield of DNA (μg/tube) | 4.3 | 9.1 | 14.8 | 20.8 | | | |
| Bacteria Containing pPic-91C | Bacteria Volume (ml) | 1.0 | 2.0 | 3.0 | 4.0 | 60 μl | 4 | FIG. 2-2 |
| | $OD_{260}$ | 0.093 | 0.208 | 0.292 | 0.416 | | | |
| | $OD_{280}$ | 0.054 | 0.116 | 0.170 | 0.237 | | | |
| | $OD_{260}/OD_{280}$ | 1.72 | 1.79 | 1.72 | 1.76 | | | |
| | Concentration (ng/μl) | 4.0 | 10.0 | 14.0 | 20.0 | | | |
| | Production Yield of DNA (μg/tube) | 1.0 | 2.4 | 3.4 | 4.8 | | | |
| *Pseudomonas aeruginosa* | Bacteria Volume (ml) | 1.0 | 2.0 | 3.0 | 4.0 | 60 μl | 4 | FIG. 2-3 |
| | $OD_{260}$ | 0.166 | 0.351 | 0.478 | 0.529 | | | |
| | $OD_{280}$ | 0.101 | 0.202 | 0.262 | 0.288 | | | |
| | $OD_{260}/OD_{280}$ | 1.65 | 1.74 | 1.83 | 1.84 | | | |
| | Concentration (ng/μl) | 8.0 | 17.0 | 23.0 | 26.0 | | | |
| | Production Yield of DNA (μg/tube) | 1.9 | 4.1 | 5.5 | 6.2 | | | |
| Bacteria Containing pETc-2a | Bacteria Volume (ml) | 1.0 | 2.0 | 3.0 | 4.0 | 60 μl | 2 | FIG. 2-4 |
| | $OD_{260}$ | 0.092 | 0.141 | 0.205 | 0.246 | | | |
| | $OD_{280}$ | 0.056 | 0.087 | 0.123 | 0.140 | | | |
| | $OD_{260}/OD_{280}$ | 1.66 | 1.63 | 1.67 | 1.75 | | | |
| | Concentration (ng/μl) | 4.0 | 7.0 | 10.0 | 12.0 | | | |
| | Production Yield of DNA (μg/tube) | 0.48 | 0.84 | 1.20 | 1.40 | | | |

EXAMPLE 1-2

Purifying for Middle Amount of Super Pure Plasmid DNA

Steps of Process

Pretreatment: collect 40 ml highly copying plasmid bacteria solution cultured overnight in the LB culture medium or 100 ml lowly copying plasmid bacteria solution cultured overnight in the LB culture medium, centrifuge at ≧3000×g for 8 minutes, discard the supernatant completely. Convert the centrifuge tube on paper for several minutes, and remove the supernatant completely. Suspend the bacteria fully with 4.5 ml bacteria suspension added with RNase A1.

Attention: excessive bacteria will influence lysing and neutralizing efficiency and the production yield of plasmid DNA. If rich culture medium is used, the volume of the bacteria solution should be reduced half or more.

Attention: Small bacteria clump should not be remained; otherwise, lysing of bacteria will be affected.

Add 4.5 ml lysing solution, reverse and blend for 4~6 times gently and fully, and the step should last for no longer than 5 minutes.

Attention: violently shaking is forbidden, otherwise, genomic DNA will be contaminated.

1) Agglutination: add 8 ml buffer cooled at 4° C. previously (480 g cesium chloride, 18 g monosodium orthophosphate, and add water to 1 liter; 36~45 g ammonium acetate), reverse gently and fully, and homogenize until the precipitation becomes a compact agglutination clump.

Attention: after the buffer is added, blending should be started immediately so as to prevent forming local agglutination clump; violently shaking is forbidden, otherwise, genomic DNA will be contaminated.

2) Phase isolation: add 12 ml phase isolation solution cooled at 4° C. previously (ethanol: isopropyl alcohol=5:1), reverse for 10 times gently, blend with more strength for several times so as to make the solution become a turbid emulsion, and centrifuge at ≧10000×g and at 4° C. for 8 minutes. Thus, upper phase, lower phase, phase middle and precipitation are formed. Wherein, plasmid DNA waits for being purified in the lower phase.

EXAMPLE 2

Phase Isolation for the Object of Purifying Genomic DNA

Lysing solution: 1%~2% CTAB and/or 0~7M guanidine hydrochloride, 100 mM Tris, pH 8.5, 1M NaCl, 10 mM EDTA, 0.5% 2-mercaptoethanol;

Pretreatment: generally, one of CTAB and guanidine hydrochloride can lyse the cells and release genomic DNA effectively. If CTAB and guanidine hydrochloride are used together, the speed and efficiency of lysing cells/tissue will be promoted to a great extent. For plant and animal tissue, after the tissue is ground in liquid nitrogen, it is preferably dissolved with 2% CTAB, and then heated in water bath of 60~80° C. for 10~60 minutes so as to release genomic DNA entirely. If genomic DNA releasing requires to be improved by heating, guanidine hydrochloride should not be added in the lysing solution, because guanidine hydrochloride will cause hydrolysis of genomic DNA at high temperature. When extracting genomic DNA from blood cells, it should not heat; otherwise, gel-agglutination clump will be formed, thus the extraction of DNA will be affected severely.

The lysing solution is alkaline, and pH is preferably 8.0~9.0. If pH is smaller than 7, it is easy for genomic DNA to become phase middle precipitation together with protein and this will severely influence the production yield of DNA.

Agglutination: add buffer (330 g ammonium sulfate, 290 g guanidine hydrochloride, and add water to 1 liter) to facilitate protein flocculating and precipitating.

Phase isolation: add phase isolation solution (anhydrous ethanol: isopropyl alcohol (v/v)=1:1, 2~5 ml/l glacial acetic acid) into the system, two phases are formed immediately, CTAB, heme, chlorophyll and lipid are extracted into the upper phase completely, and the phase isolation further facilitate the denaturation and separation of protein, make protein precipitation in the phase middle, and genomic DNA is distributed into the lower phase.

Preparing of Small Amount of the Genome DNA

| Sample and Its Dosage | | The value of OD of genomic DNA | | | | | Eluting Volume | Diluting Times | Electrophoretogram |
|---|---|---|---|---|---|---|---|---|---|
| 15 mg little white mouse muscle | | 1 | 2 | 3 | 4 | 5 | 60 μl | 3.5 | FIG. 3-1 |
| | $OD_{260}$ | 0.520 | 0.459 | 0.408 | 0.416 | 0.365 | | | |
| | $OD_{280}$ | 0.302 | 0.248 | 0.223 | 0.225 | 0.199 | | | |
| | $OD_{260}/OD_{280}$ | 1.73 | 1.85 | 1.83 | 1.85 | 1.84 | | | |
| | Concentration (ng/μl) | 26.0 | 23.0 | 20.4 | 20.8 | 18.3 | | | |
| | Production Yield of DNA (μg/tube) | 5.5 | 4.8 | 4.3 | 4.4 | 3.8 | | | |
| Culturing cells | | 1 | 2 | 3 | 4 | 5 | 60 μl | 7 | FIG. 3-2 |
| | $OD_{260}$ | 0.696 | 0.725 | 0.562 | 0.718 | 0.620 | | | |
| | $OD_{280}$ | 0.377 | 0.380 | 0.302 | 0.380 | 0.329 | | | |
| | $OD_{260}/OD_{280}$ | 1.85 | 1.91 | 1.86 | 1.89 | 1.88 | | | |
| | Concentration (ng/μl) | 34.8 | 36.3 | 28.1 | 35.9 | 31.0 | | | |
| | Production Yield of DNA (μg/tube) | 14.6 | 15.2 | 11.8 | 15.1 | 13.0 | | | |
| 100 mg holly leaf | | 1 | 2 | 3 | 4 | 5 | 60 μl | 3.5 | FIG. 3-3 |
| | $OD_{260}$ | 1.114 | 1.016 | 1.049 | 1.030 | 1.232 | | | |
| | $OD_{280}$ | 0.600 | 0.550 | 0.566 | 0.557 | 0.668 | | | |
| | $OD_{260}/OD_{280}$ | 1.86 | 1.85 | 1.85 | 1.85 | 1.85 | | | |
| | Concentration (ng/μl) | 55.7 | 50.8 | 52.5 | 51.5 | 61.6 | | | |
| | Production Yield of DNA (μg/tube) | 11.7 | 10.7 | 11.0 | 10.8 | 12.9 | | | |
| 80 μl pig whole blood | | 1 | 2 | 3 | 4 | 5 | 60 μl | 2.5 | FIG. 3-4 |
| | $OD_{260}$ | 0.329 | 0.279 | 0.362 | 0.309 | 0.367 | | | |
| | $OD_{280}$ | 0.191 | 0.155 | 0.206 | 0.167 | 0.216 | | | |
| | $OD_{260}/OD_{280}$ | 1.72 | 1.80 | 1.76 | 1.84 | 1.70 | | | |
| | Concentration (ng/μl) | 16.5 | 14.0 | 18.1 | 15.5 | 18.4 | | | |
| | Production Yield of DNA (μg/tube) | 2.5 | 2.1 | 2.7 | 2.3 | 2.8 | | | |
| pUC-19 bacteria | | 1 | 2 | 3 | 4 | 5 | 60 μl | 7 | FIG. 3-5 |
| | $OD_{260}$ | 0.735 | 0.761 | 0.683 | 0.612 | 0.585 | | | |
| | $OD_{280}$ | 0.382 | 0.393 | 0.353 | 0.318 | 0.303 | | | |
| | $OD_{260}/OD_{280}$ | 1.93 | 1.94 | 1.93 | 1.92 | 1.93 | | | |
| | Concentration (ng/μl) | 36.8 | 38.0 | 34.2 | 30.6 | 29.3 | | | |
| | Production Yield of DNA (μg/tube) | 15.5 | 15.9 | 14.3 | 12.9 | 12.3 | | | |

EXAMPLE 3

Phase Isolation for the Object of Purifying Total RNA lysing solution: 7M guanidine hydrochloride or 4M guanidinium isothiocyanate, 5 mM $Na_2HPO_4$, 10 mM EDTA, 10 g ammonium acetate, 0.1% 2-mercaptoethanol, pH 6.3~6.8;

Buffer: 398 g ammonium sulfate, 96 g guanidine hydrochloride, 4 g $Na_2HPO_4 \cdot 12H_2O$, and add water to 1 liter.

Pretreatment: 2-mercaptoethanol can prevent the oxide in the cells damaging RNA molecule. EDTA is complex agent of $Ca^{2+}$ and $Mg^{2+}$ and can reduce the influence of $Ca^{2+}$ and $Mg^{2+}$ in the cellsto isolation of RNA.

1) Agglutination: add buffer (protein flocculation solution) which contains 398 g/l ammonium sulfate, 1M guanidine hydrochloride, and 12 mM sodium orthophosphate dimetallic. The ammonium sulfate in the solution makes protein flocculate and separate out, forms insoluble composition with long chain genomic DNA, and makes preparation for the two phases occurring later. In the step, the concentration of the ammonium sulfate is crucial. Certain concentration is required for denaturing protein so as to insure forming of the phases afterwards and keeps the solubility of RNA. If the concentration is too high, RNA will denature and separate out together with protein; if too low, the denaturation of protein will not be achieved and two-phase system will not be formed in the sequent process. Add certain amount of guanidine hydrochloride into the protein flocculation solution will further improve the dissociation of RNA and make RNA not to be enclosed in protein precipitation. The use of sodium orthophosphate dimetallic keeps the range of the pH of the solution system at 6.8±0.05. Too low pH will influence the production yield of RNA, but when the pH is higher than or equal to 7.0, too much genomic DNA will dissolve in the lower phase resulting in a viscosity increase in the solution, which makes RNA molecule difficult to precipitate or genomic DNA contaminated.

Pre-phase isolation and purifying: after adding isobutyl alcohol into the pretreated solution, protein further denatures and separates out, and RNA is still in dissociation. After centrifuge, most of protein becomes phase middle precipitation together with genomic DNA and is isolated and removed. The fatsoluble components are extracted into the isobutyl alcohol and discarded. Then the lower phase is taken into the 2) step of phase isolation.

2) Phase isolation: after adding phase isolation solution (ethanol: isopropyl alcohol (v/v)=6:7), two phases form, and water is extracted into the organic phase (the upper phase). This makes RNA molecule concentrate in the lower phase and makes the concentration of ammonium sulfate in the lower phase be in saturation. Total RNA and dissociative DNA (small segment genomic DNA, mitochondrial DNA, transfected eukaryotic vector, viral DNA molecule) are contained in the lower phase. DNA molecule is still in dissociation in the highly saturated ammonium sulfate solution (the lower phase), and RNA molecule is insoluble in the ammonium sulfate with high saturation and $\geq 5M$ ammonium acetate. However, $NH_4Ac$ and ethanol, isopropyl alcohol can be dissolved in each other, and they cannot be used as phase forming medium and only ammonium sulfate that is highly insoluble in ethanol/isopropyl alcohol can be chosen as the phase forming medium.

Preparation for Small Amount of Culturing Cells, Bacteria, Yeast, and Plant and Animal Tissue RNA

| Sample and Its Dosage | | The value of OD of RNA | | | | Eluting Volume (µl) | Diluting Times | Electrophoretogram |
|---|---|---|---|---|---|---|---|---|
| $0.4 \times 10^4$ culturing cells | | 1 | 2 | 3 | 4 | 40 | 10× | FIG. 4-1 |
| | $OD_{260}$ | 0.848 | 0.852 | 1.025 | 1.031 | | | |
| | $OD_{280}$ | 1.396 | 0.416 | 0.502 | 0.486 | | | |
| | $OD_{260}/OD_{280}$ | 2.14 | 2.05 | 2.04 | 2.12 | | | |
| | Concentration (ng/µl) | 33.92 | 34.08 | 41.00 | 41.24 | | | |
| | Production Yield of RNA (µg/tube) | 13.57 | 13.63 | 16.40 | 16.49 | | | |
| 200 mg holly leaf | | 1 | 2 | 3 | 4 | 200 | 20× | FIG. 4-2 |
| | $OD_{260}$ | 1.543 | 1.421 | 1.444 | 1.514 | | | |
| | $OD_{280}$ | 0.721 | 0.663 | 0.794 | 0.767 | | | |
| | $OD_{260}/OD_{280}$ | 2.14 | 2.14 | 1.82 | 1.97 | | | |
| | Concentration (ng/µl) | 61.72 | 56.84 | 57.76 | 65.60 | | | |
| | Production Yield of RNA (µg/tube) | 246.9 | 227.4 | 237.0 | 262.4 | | | |
| 250 µl little white mouse blood | | 1 | 2 | 3 | 4 | 40 | 20× | FIG. 4-3 |
| | $OD_{260}$ | 0.610 | 0.639 | 0.665 | 0.589 | | | |
| | $OD_{280}$ | 0.338 | 0.355 | 0.375 | 0.326 | | | |
| | $OD_{260}/OD_{280}$ | 1.81 | 1.80 | 1.77 | 1.81 | | | |
| | Concentration (ng/µl) | 24.4 | 25.6 | 26.6 | 23.5 | | | |
| | Production Yield of RNA (µg/tube) | 19.52 | 20.45 | 21.28 | 18.85 | | | |
| 3 ml bacteria | | pCwp1f1 | | pUC-19 | | 40 | 40× | FIG. 4-4 |
| | $OD_{260}$ | 0.198 | 0.139 | 0.370 | 0.292 | | | |
| | $OD_{280}$ | 0.104 | 0.072 | 0.198 | 0.154 | | | |

-continued

| Sample and Its Dosage | The value of OD of RNA | | | | | Eluting Volume (μl) | Diluting Times | Electrophoretogram |
|---|---|---|---|---|---|---|---|---|
| | $OD_{260}/OD_{280}$ | 1.91 | 1.94 | 1.86 | 1.89 | | | |
| | Concentration (ng/μl) | 7.92 | 5.56 | 14.80 | 11.68 | | | |
| | Production Yield of RNA (μg/tube) | 12.67 | 8.90 | 23.68 | 18.69 | | | |
| 4 ml yeast | | 1 | 2 | 3 | 4 | 60 | 60× | FIG. 4-5(a) and FIG. 4-5(b) |
| | $OD_{260}$ | 1.022 | 1.092 | 1.496 | 1.526 | | | |
| | $OD_{280}$ | 0.576 | 0.585 | 1.808 | 0.801 | | | |
| | $OD_{260}/OD_{280}$ | 1.77 | 1.87 | 1.85 | 1.90 | | | |
| | Concentration (ng/μl) | 40.88 | 43.68 | 59.84 | 61.04 | | | |
| | Production Yield of RNA (μg/tube) | 147.17 | 157.25 | 215.42 | 219.74 | | | |
| 100 mg mouse liver | | 1 | 2 | 3 | 4 | 60 | 60× | FIG. 4-6 |
| | $OD_{260}$ | 1.188 | 1.130 | 1.693 | 0.751 | | | |
| | $OD_{280}$ | 0.620 | 0.586 | 0.908 | 0.394 | | | |
| | $OD_{260}/OD_{280}$ | 1.92 | 1.93 | 1.86 | 1.91 | | | |
| | Concentration (ng/μl) | 47.52 | 45.20 | 67.72 | 30.04 | | | |
| | Production Yield of RNA (μg/tube) | 171.1 | 162.7 | 243.8 | 108.14 | | | |
| 100 mg mouse brain | | 1 | 2 | 3 | 4 | 40 | 40× | FIG. 4-7 |
| | $OD_{260}$ | 1.279 | 1.244 | 0.611 | 1.472 | | | |
| | $OD_{280}$ | 0.692 | 0.656 | 0.322 | 0.781 | | | |
| | $OD_{260}/OD_{280}$ | 1.85 | 1.90 | 1.90 | 1.88 | | | |
| | Concentration (ng/μl) | 51.16 | 49.76 | 24.44 | 58.88 | | | |
| | Production Yield of RNA (μg/tube) | 81.86 | 79.62 | 19.55 | 94.21 | | | |

EXAMPLE 4

Phase Isolation for the Object of Purifying Protein

Agglutination solution: ammonium sulfate with 90%~100% saturation;

Take 0.5 ml solution containing protein, add it into a 2 ml centrifuge tube, add 0.2 ml agglutination solution, homogenize and place it in the ice bath for 5 minutes; add 0.65 ml phase isolation solution cooled at 4° C. previously (ethanol:isopropyl alcohol=1:5), and homogenize immediately; centrifuge at 12000×g at 4° C. for 1 minute, then protein precipitates on the interface of the two phases.

The invention claimed is:

1. A phase isolation process for biomacromolecule components, comprising treating a sample comprising a substance to be isolated, wherein said substance is plasmid DNA, said process comprising:
   1) Preparing a buffer by dissolving 380 g -480 g ammonium sulfate or cesium chloride, and 14 g -18 g monosodium orthophosphate in water, and bringing the volume to 1 liter;
   2) Adding a sufficient amount of the buffer from step (1) to said sample and homogenizing, so as to carry out agglutination;
   3) Adding a phase isolation solution comprising a mixture of ethanol and isopropyl alcohol and the ratio of volume is ethanol:isopropyl alcohol=2:1-10:1, homogenizing, and centrifuging to form an upper phase, a lower phase, phase middle precipitation, and lower phase precipitation; wherein lipid is in the upper phase, protein precipitates in the phase middle, DNA plasmid, viral nucleic acid, mitochondrial DNA are in the lower phase, and total RNA precipitates in the lower phase; and genomic DNA precipitates in the lower phase or in the phase middle together with protein.

2. The phase isolation process as recited in claim 1, the buffer further comprises 10 g-60 g ammonium acetate.

3. A phase isolation process for biomacromolecule components, comprising treating a sample comprising a substance to be isolated, wherein said substance is genomic DNA, said process comprising:
   1) Preparing a buffer by dissolving 330 g ammonium sulfate in water, and bringing the volume to 1 liter;
   2) Adding a sufficient amount of the buffer from step (1) to said sample and homogenizing, so as to carry out agglutination;
   3) Adding a phase isolation solution comprising a mixture of anhydrous ethanol and isopropyl alcohol and the ratio of volume is anhydrous ethanol:isopropyl alcohol=0.5:1-2:1, homogenizing, and centrifuging to form an upper phase, a lower phase, phase middle precipitation, and lower phase precipitation; wherein lipid is in the upper phase, protein precipitates in the phase middle, DNA plasmid, viral nucleic acid, mitochondrial DNA are in the lower phase, and total RNA precipitates in the lower phase; and genomic DNA precipitates in the lower phase or in the phase middle together with protein.

4. The phase isolation process as recited in claim 3, wherein the buffer further comprises 290 g guanidine hydrochloride; and the phase isolation solution further comprises 2-5 ml/1 glacial acetic acid.

5. A phase isolation process for biomacromolecule components, comprising treating a sample comprising a substance to be isolated, wherein said substance is total RNA, said process comprising:
1) Preparing a buffer by dissolving 398 g ammonium sulfate, 96 g guanidine hydrochloride, 4 g Na$_2$HPO$_4$.12H$_2$O in water, and bringing the volume to 1 liter;
2) Adding a sufficient amount of the buffer from step (1) to said sample and homogenizing, so as to carry out agglutination;
Adding a phase isolation solution comprising a mixture of ethanol and isopropyl alcohol and the ratio of volume is ethanol:isopropyl alcohol=7:5-7:7, homogenizing, and centrifuging to form an upper phase, a lower phase, phase middle precipitation, and lower phase precipitation; wherein lipid is in the upper phase, protein precipitates in the phase middle, DNA plasmid, viral nucleic acid, mitochondrial DNA are in the lower phase, and total RNA precipitates in the lower phase; and genomic DNA precipitates in the lower phase or in the phase middle together with protein.

6. A phase isolation process for biomacromolecule components, comprising treating a sample comprising a substance to be isolated, wherein said substance is protein, said process comprising:
1) Preparing a buffer comprising ammonium sulfate of 90%-100% saturation, 80 mM monosodium orthophosphate, and 80 mM sodium orthophosphate dimetallic;
2) Adding a sufficient amount of the buffer from step (1) to said sample and homogenizing, so as to carry out agglutination;
3) Adding a phase isolation solution comprising a mixture of anhydrous ethanol and isopropyl alcohol, and the ratio of volume is anhydrous ethanol:isopropyl alcohol=1:3-1:10, and between 2-5 ml/l glacial acetic acid, homogenizing, and centrifuging to form an upper phase, a lower phase, phase middle precipitation, and lower phase precipitation; wherein lipid is in the upper phase, protein precipitates in the phase middle, DNA plasmid, viral nucleic acid, mitochondrial DNA are in the lower phase, and total RNA precipitates in the lower phase; and genomic DNA precipitates in the lower phase or in the phase middle together with protein.

* * * * *